United States Patent
Kim

(10) Patent No.: US 9,395,328 B2
(45) Date of Patent: Jul. 19, 2016

(54) APPARATUS FOR DETECTING SODIUM IN A LIQUID

(71) Applicant: Nam Tae Kim, Yeonje-gu Busan (KR)

(72) Inventor: Nam Tae Kim, Yeonje-gu Busan (KR)

(73) Assignee: INJE UNIVERSITY INDUSTRY-ACADEMIC COOPERATION FOUNDATION, Gyeongsangnam-Do (KR)

( * ) Notice: Subject to any disclaimer, the term of this patent is extended or adjusted under 35 U.S.C. 154(b) by 0 days.

(21) Appl. No.: 14/118,970

(22) PCT Filed: May 20, 2013

(86) PCT No.: PCT/KR2013/004384
§ 371 (c)(1),
(2) Date: Nov. 20, 2013

(87) PCT Pub. No.: WO2014/017737
PCT Pub. Date: Jan. 30, 2014

(65) Prior Publication Data
US 2015/0122648 A1   May 7, 2015

(30) Foreign Application Priority Data
Jul. 26, 2012   (KR) .................. 10-2012-0081893

(51) Int. Cl.
*G01N 27/416* (2006.01)
*G01N 27/06* (2006.01)
*G01N 33/18* (2006.01)

(52) U.S. Cl.
CPC ............ *G01N 27/4166* (2013.01); *G01N 27/06* (2013.01); *G01N 33/18* (2013.01)

(58) Field of Classification Search
CPC ... G01N 27/06; G01N 27/416; G01N 27/301; G01N 27/302; G01N 27/333; G01N 33/18
See application file for complete search history.

(56) References Cited

U.S. PATENT DOCUMENTS

2011/0042238 A1*   2/2011   Bhavaraju .............. G01N 27/49
                                                                    205/781.5

FOREIGN PATENT DOCUMENTS

| JP | 09-005283 | * | 1/1997 |
| KR | 10-2003-0020716 | * | 3/2003 |

(Continued)

OTHER PUBLICATIONS

Machine translation Mar. 30, 2016 KR10-2009-0106917.*
Machine translation Mar. 30, 2016 KR10-2003-0020716.*
(Continued)

*Primary Examiner* — Jennifer Dieterle
(74) *Attorney, Agent, or Firm* — Porzio, Bromberg & Newman, P.C.

(57) ABSTRACT

There is provided an apparatus for detecting sodium in a liquid. A concentration of a very small amount of sodium can be repeatedly and accurately measured by correcting baseline fluctuation and sodium concentration variation due to temperature variation on the basis of measured temperature and minimizing noise influence on the concentration measurement. According to the apparatus for detecting sodium in a liquid, the apparatus for detecting sodium in a liquid can accurately and repeatedly measure a concentration of a very small amount of sodium by minimizing noise and temperature variation effects on concentration measurements to ensure measurement accuracy of sodium concentration and the stability of a baseline as a measurement reference.

16 Claims, 3 Drawing Sheets

(56) References Cited

FOREIGN PATENT DOCUMENTS

| KR | 10-2009-0056731 | * | 6/2009 |
| KR | 10-2009-0106917 | * | 10/2009 |

OTHER PUBLICATIONS

Machine translation Mar. 30, 2016 JP 09-005283.*
Machine translation Mar. 30, 2016 KR10-2009-0056731.*

* cited by examiner

APPARATUS FOR DETECTING SODIUM IN A LIQUID

TECHNICAL FIELD

The present invention relates to an apparatus for accurately measuring a very small amount of sodium in a liquid, and more particularly, to an apparatus for detecting sodium in a liquid that repeatedly and accurately measures a very small amount of sodium in a liquid by processing a voltage output from a sodium detecting unit with low noise and compensating the processed signal on the basis of a temperature.

BACKGROUND ART

Sodium (hereinafter, including natrium) is an essential element for vital functions of all animals, but excess sodium may cause considerable side effects on a living body. Further, the sodium reacts to metal such as iron to promote corrosion of the metal.

For this reason, an existing sodium detector is used to measure and monitor purity of water for a boiler, a pollution level of drinking water, a concentration of sodium in a fluid utilization system, and the like.

In such applications, since the sodium concentration is a relatively high, the existing detector includes a sodium detecting unit that operates at room temperature and a sodium-signal processing circuit having a relatively high noise figure.

However, in the sodium detector according to the related art, there are considerable variations in measurement baseline and a measured concentration of the sodium due to influence of noises and a temperature change of a sodium detecting unit. Such variations pose problems that a measurement range of the concentration and accuracy in measurement are limited when a concentration of a very small amount of sodium in a liquid is measured. Therefore, there is a problem that the existing detector is difficult to accurately measure a very small amount of sodium in a liquid.

DISCLOSURE

Technical Problem

In order to solve the aforementioned problems of the related art, an aspect of the present invention provides an apparatus for detecting sodium in a liquid that can repeatedly and accurately measure a concentration of a very small amount of sodium by minimizing noise and temperature variation effects on measurement baseline and measured concentration of sodium.

Technical Solution

In order to achieve to the aspect, according to an aspect of the present invention, there is provided an apparatus for detecting sodium in a liquid including a sodium detecting unit that detects concentration of sodium in a liquid using a plurality of voltages; a temperature-signal processing unit that measures a temperature of the sodium detecting unit; a low-noise amplifying unit that amplifies the difference between the plurality of voltages detected by the sodium detecting unit with low noise; a filtering and amplifying unit that amplifies the low-noise signal output from the low-noise amplifying unit up to a required level and filters the amplified low-noise signal; and a signal-processing and controlling unit that calculates concentration of the sodium using the low-noise signal received from the filtering and amplifying unit and corrects the calculated concentration of the sodium on the basis of the temperature measured by the temperature-signal processing unit by referring to electrode voltages for a standard solution measured at several temperatures and stored in a memory.

The sodium detecting unit may include an inlet tube that introduces the liquid through an upper portion on one side; an outlet tube that discharges the liquid through a lower portion on the other side not facing the inlet tube; and a flow cell that is interposed between the inlet tube and the outlet tube that are formed at the upper and lower portions, has a predetermined volume of space in which the liquid is allowed to flow in a horizontal direction, and includes a sodium electrode that detects the concentration of the sodium using a voltage generated at a pair of (+) and (−) electrodes formed downward in a vertical direction from the upper portion and a reference electrode that detects a reference voltage using a voltage generated at a pair of (+) and (−) electrodes formed to be parallel with the sodium electrode at a regular distance.

The temperature-signal processing unit may include a temperature sensor that is provided at one portion in the flow cell to detect a temperature of the liquid.

The sodium detecting unit may include a flow-rate controlling device that is provided at the inlet tube or the outlet tube of the flow cell to control a flow rate of the liquid.

The temperature-signal processing unit may include a temperature-signal processing circuit that measures the temperature of the liquid in the flow cell by processing a signal from the temperature sensor and transmits the measured temperature to the signal-processing and controlling unit.

The apparatus for detecting sodium in a liquid may further include a transmission line that electrically connects the sodium detecting unit to the temperature-signal processing unit and has noise shielding capability.

The low-noise amplifying unit may include a low-noise amplifier that amplifies the difference between two output voltages of the sodium electrode and the reference electrode in the sodium detecting unit with low noise, which is determined by the sodium concentration in a liquid.

The low-noise amplifying unit may include a switching circuit that adjusts a gain of the low-noise amplifier according to a setting of the signal-processing and controlling unit to set a sodium-concentration measurement range to a desired range.

The apparatus for detecting sodium in a liquid may further include transmissions that electrically connect the sodium detecting unit to the low-noise amplifying unit and have noise shielding capability.

The filtering and amplifying unit may include a low pass filter that filters the low-noise signal output from the low-noise amplifying unit and transmits the filtered low-noise signal to the signal-processing and controlling unit.

The filtering and amplifying unit may include an intermediate amplifier that amplifies the output signal of the low-noise amplifying unit and transmits the amplified low-noise signal to the low pass filter.

The filtering and amplifying unit may include an offset adjustment circuit that adjusts an output offset of the intermediate amplifier.

The signal-processing and controlling unit may include a microcomputer that corrects the output voltage variations of the sodium electrode and the reference electrode on the basis of the measured temperature by referring to the electrode voltages for a standard solution measured at several temperatures, generates control commands, and performs signal processing.

The signal-processing and controlling unit may include a measurement-condition setting unit that sets a sodium-concentration measurement range.

The signal-processing and controlling unit may include a measurement-status display unit that displays the measured concentration of the sodium, the measured temperature, and the electrode voltage that is processed by the microcomputer.

The signal-processing and controlling unit may include a communication circuit that transmits a measured sodium concentration received from the filtering and amplifying unit or a temperature of the liquid received from the temperature-signal processing unit to an external equipment using analog or digital methods.

Effect

According to the apparatus for detecting sodium in a liquid, a concentration of a very small amount of sodium can repeatedly and accurately be measured by minimizing noise and temperature variation effects on concentration measurements to ensure measurement accuracy of sodium concentration and the stability of a baseline as a measurement reference.

BEST MODE

Hereinafter, a preferred embodiment of the present invention will be described in detail with reference to the accompanying drawings.

Figure 1:
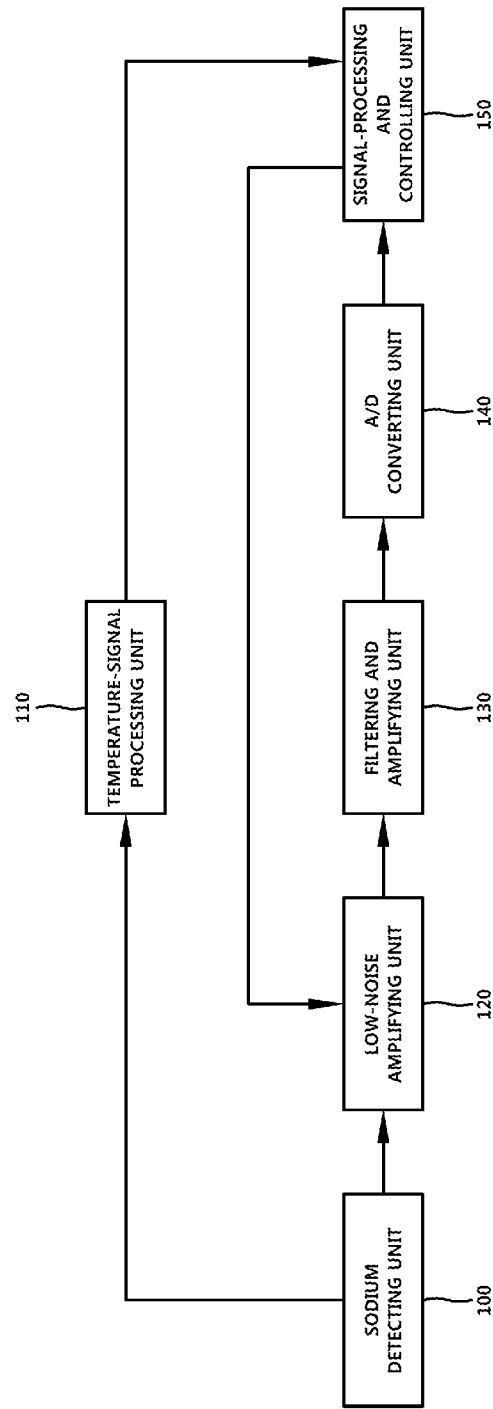
FIG. 1 is a block configuration diagram illustrating an apparatus for detecting sodium in a liquid according to a preferred embodiment of the present invention.
Figure 2:
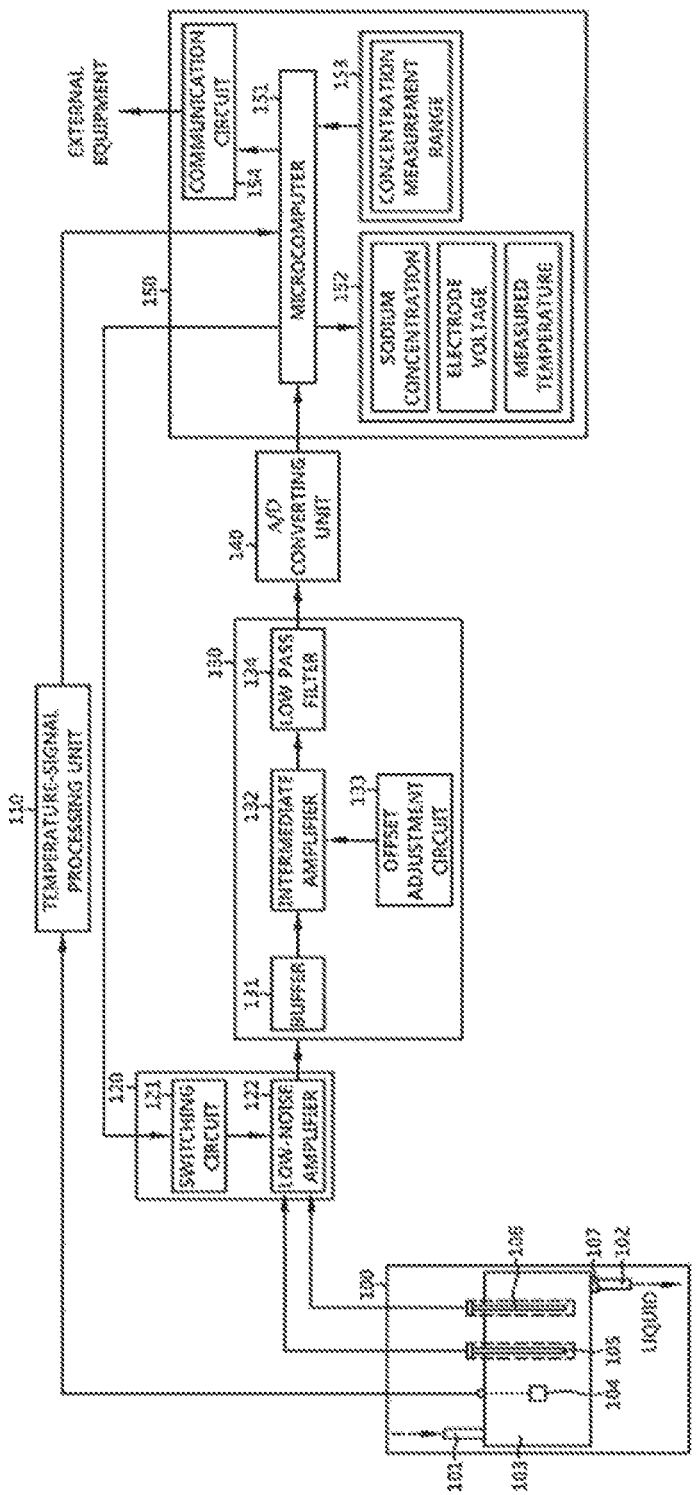
FIG. 2 is a detailed block configuration diagram illustrating the apparatus for detecting sodium in a liquid shown in FIG. 1.
Figure 3:
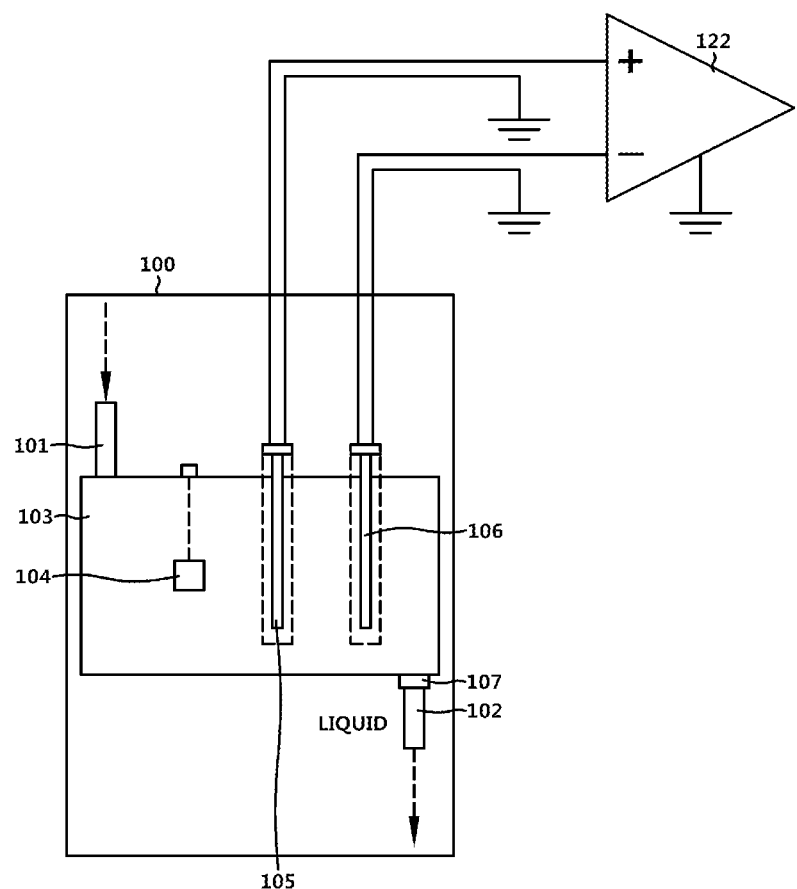
FIG. 3 is a detailed block configuration diagram illustrating a connected state of a sodium detecting unit and a low-noise amplifying unit shown in FIG. 2.

FIG. 1 is a block diagram illustrating an apparatus for detecting sodium in a liquid according to a preferred embodiment of the present invention.

As shown in the drawing, the apparatus for detecting sodium in a liquid according to the present invention includes a sodium detecting unit 100 that detects concentration of sodium in a liquid using a plurality of voltages, a temperature-signal processing unit 110 that measures a temperature of the sodium detecting unit 100, a low-noise amplifying unit 120 that amplifies the difference between the plurality of voltages detected by the sodium detecting unit 100 with low noise, a filtering and amplifying unit 130 that amplifies the low-noise signal output from the low-noise amplifying unit 120 up to a required level and filters the amplified low-noise signal, and a signal-processing and controlling unit 150 that calculates the concentration of the sodium using the low-noise signal received from the filtering and amplifying unit 130, corrects the calculated sodium concentration by referring to electrode voltages for a standard solution measured at several temperatures stored in a memory, on the basis of the temperature measured by the temperature-signal processing unit 110, generates control commands, and processes various signals.

The signal-processing and controlling unit 150 may display measurement states of the sodium according to a setting of measurement conditions and transmit the measured signals to an external equipment (not shown). Further, the apparatus for detecting sodium may further include an A/D converting unit 140 that converts an analogue signal output from the filtering and amplifying unit 130 into a digital signal and transmits the converted signal to the signal-processing and controlling unit 150.

The sodium detecting unit 100 includes an inlet tube 101, an outlet tube 102 and a flow cell 103. The inlet tube 101 introduces the liquid through an upper portion on one side, and the outlet tube 102 discharges the liquid through a lower portion on the other side not facing the input tube 101. The flow cell 103 is interposed between the inlet tube 101 and the outlet tube 102 that are formed at the upper and lower portions and has a desired volume of space in which the liquid is allowed to flow in a horizontal direction. Furthermore, the flow cell includes a sodium electrode 105 that detects the sodium concentration using a voltage generated at a pair of (+) and (−) electrodes that is formed downward in a vertical direction from an upper portion and a reference electrode 106 that detects a reference voltage using a voltage generated at a pair of (+) and (−) electrodes that is formed to be parallel with the sodium electrode 105 at a regular distance.

The sodium electrode 105 is an electrode that generates a voltage determined by the sodium concentration in a liquid, and the reference electrode 106 is an electrode that generates a reference voltage to the voltage of the sodium electrode.

The sodium detecting unit 100 may further include a flow-rate controlling device 107 that is provided at the inlet or outlet tubes 101 and 102 of the flow cell 103 and controls a flow rate of the liquid.

Moreover, a temperature sensor 104 of the temperature-signal processing unit 110 may be provided at one portion in the flow cell 103 of the sodium detecting unit 100 to detect a temperature of the liquid.

As shown in the drawings, in the sodium detecting unit 100 according to the preferred embodiment of the present invention, the sodium and reference electrodes 105 and 106 detect the sodium concentrations by introducing a liquid to be measured into the flow cell 103 through the inlet tube 101 and temporarily storing the liquid in the flow cell 103, and the liquid of which concentration has been measured is discharged to the outside of the flow cell 103 through the outlet tube 102. Here, by controlling the flow rate of the liquid by the flow-rate controlling device 107, the sodium concentration can be more accurately measured.

The (+) and (−) electrodes of the sodium electrode 105 may be made from a material that reacts to sodium ions to generate a voltage depending on the sodium concentration, and the (+) and (−) electrodes of the reference electrode 106 may be made from a material such as mercury (I) chloride (calomel) that can provide a stable reference voltage to the sodium electrode 105.

The sodium electrode 105 generates a voltage on the basis of the sodium concentration of the liquid and provides the generated voltage to the low-noise amplifying unit 120.

The reference electrode 106 generates the reference voltage and provides the reference voltage to the low-noise amplifying unit 120.

In addition, the temperature sensor 104 detects the temperature of the liquid passing through the flow cell 103. The temperature sensor 104 can accurately measure the temperature of the liquid flowing in the flow cell 103 by fixing a temperature sensor such as a thermistor to the flow cell 103.

In order to minimize the influence of noises, the sodium and reference electrodes 105 and 106 may be electrically connected to the low-noise amplifying unit 120 using transmission lines (not shown) with noise shielding capability such as a coaxial cable.

In order to compensate output voltage variations of the sodium and reference electrodes 105 and 106 due to temperature variation, the temperature-signal processing unit 110 processes a signal from the temperature sensor 104 and transmits the processed signal to the signal-processing and controlling unit 150. The temperature signal from the temperature-signal processing unit 110 allows a user to know a liquid temperature at the time of measuring the sodium, and is used as data for compensating variations of a measurement baseline and the measured sodium concentration due to temperature variation, in case that the temperature of a measurement environment varies.

As shown in the drawings, the temperature-signal processing unit 110 according to the preferred embodiment of the present invention serves to process appropriately the temperature signal detected by the temperature sensor 104, transmit the processed signal to the signal-processing and controlling unit 150, and allow a user to know a temperature of a measurement environment.

Since the voltages of the sodium and reference electrodes 105 and 106 are a function of a liquid temperature as well as a sodium concentration, when the outputs of the electrodes vary due to temperature variation of the measurement environment, the signal-processing and controlling unit 150 corrects the electrode voltages on the basis of measured temperature by referring to electrode voltages for the standard solution measured at several temperatures and stored in the memory (not shown). Thereby, the apparatus for detecting sodium in a liquid can repeatedly and accurately measure a concentration of a very small amount of sodium regardless of temperature variation of a measurement environment.

The electrode voltages for the standard solution measured at several temperatures are the voltages that were previously obtained by several experiments and calculations, and may be stored in a microcomputer 151 or in a typical memory provided at the outside of the microcomputer 151 in the form of a look-up table or a modeled function.

In order to minimize the influence of noises and interferences, the temperature-signal processing unit 110 may be electrically connected to the temperature sensor 104 by using a transmission line (not shown) with noise shielding capability such as a coaxial cable.

The low-noise amplifying unit 120 includes a low-noise amplifier 122 that amplifies the difference between two output voltages of the sodium electrode 105 and the reference electrode 106 in the sodium detecting unit 100 with low noise and a switching circuit 121 that adjusts a gain of the low-noise amplifier 122 according to a setting of the signal-processing and controlling unit 150 to set a concentration measurement range to a desired range. Here, in order to improve measurement sensitivity, the circuit elements of the low-noise amplifying unit 120 are preferably configured using low-noise elements.

As shown in the drawings, the low-noise amplifying unit 120 according to the preferred embodiment of the present invention amplifies the difference between the output voltages from the sodium detecting unit 100 with low noise, which is determined by the sodium concentration in a liquid, so that the filtering and amplifying unit 130 can easily process the concentration of a very small amount of sodium.

As mentioned above, the low-noise amplifier 122 amplifies the output signals of the sodium detecting unit 100 with low noise, and the switching circuit 121 adjusts the gain of the low-noise amplifier 122 to change a sodium-concentration measurement range.

The switching circuit 121 can be controlled by the signal-processing and controlling unit 150. However, when the concentration measurement range is fixed to a predetermined range, the switching circuit 121 may not be provided.

If the low-noise amplifying unit 120 is configured using the low-noise elements, the measurement sensitivity is improved, and the apparatus for detecting sodium in a liquid according to the present invention can more conveniently measure the concentration of the very small amount of sodium thereby. The low-noise amplifier 122 serves as a difference amplifier that amplifies the voltage difference between the sodium and reference electrodes 105 and 106.

The filtering and amplifying unit 130 includes a buffer 131 that removes impedance interference, an intermediate amplifier 132 that amplifies an output voltage of the buffer 131, an offset adjustment circuit 133 that adjusts an output offset level of the intermediate amplifier 132, and a low pass filter 134 that filters the output signal of the intermediate amplifier 132 and provides the filtered output signal to the A/D converting unit 140. Since the filtering and amplifying unit 130 reduces a noise bandwidth to enhance signal-to-noise ratio (SNR) of the apparatus for detecting sodium in a liquid, it is effective to measure the concentration of the very small amount of sodium.

As shown in the drawings, the filtering and amplifying unit 130 according to the preferred embodiment of the present invention includes the buffer 131, the intermediate amplifier 132, the offset adjustment circuit 133 and the low pass filter 134, and serves to effectively detect the concentration of the small amount of sodium by suppressing noise power.

The buffer 131 provides a very high input impedance and a very low output impedance. Therefore, the low-noise amplifier 122 can stably amplify a signal regardless of a variation in its output impedance, and the intermediate amplifier 132 can also stably amplify a signal regardless of a variation in its input impedance.

In order to maintain the output signal level of the low-noise amplifying unit 120 within an input range of the A/D converting unit 140, the intermediate amplifier 132 amplifies the voltage signal from the low-noise amplifying unit 120 and the offset adjustment circuit 133 adjusts the output offset of the intermediate amplifier.

The low pass filter 134 filters the output signal of the intermediate amplifier 132 with an appropriate frequency bandwidth to accommodate the concentration signal and remove noises and interferences outside the frequency bandwidth. Since the SNR of the apparatus for detecting sodium in a liquid is enhanced by removing the noises and interference signals, the apparatus for detecting sodium in a liquid can accurately measure the concentration of the very small amount of sodium.

Since the low pass filter 134 in the filtering and amplifying unit 130 can also have an appropriate gain, the intermediate amplifier 132 may not be provided, and the offset adjustment circuit 133 may be provided at the low-noise amplifier 122 in the case.

The A/D converting unit 140 is an apparatus configured to convert a conventional analog signal into a digital signal to process a signal from the filtering and amplifying unit 130 in a digital type.

The signal-processing and controlling unit 150 includes a measurement-condition setting unit 153, a measurement-status display unit 152, a microcomputer 151, and a communication circuit 154. The measurement-condition setting unit 153 sets a sodium-concentration measurement range of the apparatus for detecting sodium in a liquid, and the measurement-status display unit 152 displays the measured concentration of the sodium, the temperature of the liquid, and the electrode voltage according to a setting of the measurement-condition setting unit 153 on a display device (not shown) such as LCD. The microcomputer 151 corrects voltage variation between the sodium and reference electrodes 105 and 106 due to temperature variation by referring to the electrode voltages for a standard solution measured at several temperatures stored in the memory, processes signals, and generates control commands. The communication circuit 154 transmits the measured signals to an external equipment (not shown) in an analogue or digital format.

Although it is not specifically shown in the drawings, the measurement-condition setting unit 153 in the signal-processing and controlling unit 150 according to the preferred embodiment of the present invention includes selection buttons that select a concentration measurement range, up/down buttons that adjust a value of an item selected by the selection buttons, and an enter button that sets the value input by the up/down buttons as a final value. The measurement-condition setting unit 153 transmits the concentration measurement range input from the buttons to the microcomputer 151.

In order to set the concentration measurement range input from the measurement-condition setting unit 153, the microcomputer 151 in the signal-processing and controlling unit 150 controls the gain of the low-noise amplifier 122 by transmitting a command corresponding to the range input from the measurement-condition setting unit 153 to the switching circuit 121 in the low-noise amplifying unit 120, so that the concentration measurement range of the apparatus for detecting sodium in a liquid is set to the range input by the setting buttons. Further, the microcomputer 151 corrects a voltage variation between the sodium and reference electrodes 105 and 106 due to temperature variation of the measurement environment.

In particular, on the basis of measured temperature, the microcomputer 151 corrects the output voltage variation between the sodium electrode 105 and the reference electrode 106 due to temperature variation by referring to the electrode voltages for the standard solution measured at several temperatures stored in the memory and generates gain control commands to the low-noise amplifying unit 120.

As described above, since the voltages of the sodium and reference electrodes 105 and 106 vary depending on a liquid temperature even at the same sodium concentration, if the temperature of the measurement environment varies, the output voltages of the electrodes vary with the temperature. Accordingly, on the basis of the temperature measured from the temperature-signal processing unit 110, the microcomputer 151 corrects the voltage variance between the electrodes 105 and 106 due to temperature variation by referring to the electrode voltages for a standard solution measured at several temperatures. Because such corrections stabilize a measurement baseline as a reference of the measurement, the apparatus for detecting sodium in a liquid can accurately measure the concentration of the very small amount of sodium. In addition, the microcomputer 151 can perform signal processing for measurement-status display, communications to an external equipment (not shown), and so on.

The measurement-status display unit 152 in the signal-processing and controlling unit 150 displays the sodium concentrations, the measured temperature, and the electrode voltage that is processed by the microcomputer 151 on the display device such as LCD, so that a user of the apparatus for detecting sodium in a liquid can easily check the sodium measurement conditions and status. Here, the electrode voltage is a voltage between the sodium electrode 105 and the reference electrode 106 that is determined by the sodium concentration in a liquid and corrected using measured temperature.

The communication circuit 154 in the signal-processing and controlling unit 150 is an apparatus configured to transmit a measured sodium concentration or a measured temperature of the liquid to an external equipment (not shown) using analog or digital methods.

Therefore, according to the apparatus for detecting sodium in a liquid of the present invention having the configuration described above, the apparatus for detecting sodium in a liquid can accurately and repeatedly measure the concentration of the very small amount of sodium by minimizing noise and temperature effects on the measurement of sodium concentration to ensure the accuracy of a concentration measurement and the stability of baseline as a measurement reference.

Embodiments described in the specifications and configurations illustrated in the drawings are merely a preferred embodiment, and do not wholly represent the technical sprit of the present invention. Therefore, it should be appreciated that various modifications and equivalents to these embodiments are possible at the time of filing the present application. Therefore, the present invention is not limited to the embodiments, and it will be apparent to those skilled in the art that various modifications can be made without departing from the gist of the present invention, as defined in the appended claims.

INDUSTRIAL APPLICABILITY

According to the apparatus for detecting sodium in a liquid, a concentration of a very small amount of sodium can be repeatedly measured with high accuracy by minimizing noise and temperature variation effects on the measurement of sodium concentration to ensure the accuracy of concentration measurement and the stability of baseline as a measurement reference.

The invention claimed is:

1. An apparatus for detecting sodium in a liquid comprising:
    a sodium detecting unit configured to detect concentration of sodium in a liquid using a plurality of voltages;
    a temperature-signal processing unit configured to measure a temperature of the sodium detecting unit;
    a low-noise amplifying unit configured to amplify the difference between the plurality of voltages detected by the sodium detecting unit with low noise;
    a filtering and amplifying unit configured to amplify the low-noise signal output from the low-noise amplifying unit up to a required level and filters the amplified low-noise signal; and
    a signal-processing and controlling unit configured to calculate the concentration of the sodium using the low-noise signal received from the filtering and amplifying unit and corrects the calculated concentration of the sodium on the basis of the temperature measured by the temperature-signal processing unit by referring to electrode voltages for a standard solution measured at several temperatures and stored in a memory.

2. The apparatus for detecting sodium in a liquid according to claim 1,
    wherein the sodium detecting unit includes:
    an inlet tube that introduces the liquid through an upper portion on one side;
    an outlet tube configured to discharge the liquid through a lower portion on the other side not facing the inlet tube; and
    a flow cell that is interposed between the inlet tube and the outlet tube that are formed at the upper and lower portions, has a predetermined volume of space in which the liquid is allowed to flow in a horizontal direction, and includes a sodium electrode configured to detect the concentration of the sodium using a voltage generated at a pair of (+) and (−) electrodes formed downward in a vertical direction from the upper portion and a reference electrode configured to detect a reference voltage using a voltage generated at a pair of (+) and (−) electrodes formed to be parallel with the sodium electrode at a regular distance.

3. The apparatus for detecting sodium in a liquid according to claim 2, wherein the temperature-signal processing unit includes a temperature sensor that is provided at one portion of the flow cell to detect a temperature of the liquid.

4. The apparatus for detecting sodium in a liquid according to claim 2, wherein the sodium detecting unit includes a flow-rate controlling device that is provided at the inlet tube or the outlet tube of the flow cell to control a flow rate of the liquid.

5. The apparatus for detecting sodium in a liquid according to claim 3, wherein the temperature-signal processing unit includes a temperature-signal processing circuit configured to measure the temperature of the liquid in the flow cell by processing a signal from the temperature sensor and transmits the measured temperature to the signal-processing and controlling unit.

6. The apparatus for detecting sodium in a liquid according to claim 1, further comprising:
a transmission line configured to electrically connect the sodium detecting unit to the temperature-signal processing unit and has noise shielding capability.

7. The apparatus for detecting sodium in a liquid according to claim 1, wherein the low-noise amplifying unit includes a low-noise amplifier configured to amplify the difference between two output voltages of the sodium electrode and the reference electrode in the sodium detecting unit with low noise.

8. The apparatus for detecting sodium in a liquid according to claim 7, wherein the low-noise amplifying unit includes a switching circuit configured to adjust a gain of the low-noise amplifier according to a setting of the signal-processing and controlling unit to set a sodium-concentration measurement range to a desired range.

9. The apparatus for detecting sodium in a liquid according to claim 1, further comprising:
transmission lines configured to electrically connect the sodium detecting unit to the low-noise amplifying unit and have noise shielding capability.

10. The apparatus for detecting sodium in a liquid according to claim 1, wherein the filtering and amplifying unit includes a low pass filter configured to filter the low-noise signal output from the low-noise amplifying unit and transmits the filtered low-noise signal to the signal-processing and controlling unit.

11. The apparatus for detecting sodium in a liquid according to claim 10, wherein the filtering and amplifying unit includes an intermediate amplifier configured to amplify the low-noise signal from the low-noise amplifying unit and transmits the amplified low-noise signal to the low pass filter.

12. The apparatus for detecting sodium in a liquid according to claim 11, wherein the filtering and amplifying unit includes an offset adjustment circuit configured to adjust an output offset of the intermediate amplifier.

13. The apparatus for detecting sodium in a liquid according to claim 2, wherein the signal-processing and controlling unit includes a microcomputer configured to correct the output voltage variation between the sodium electrode and the reference electrode due to temperature variance on the basis of the measured temperature by referring to the electrode voltages for the standard solution measured at several temperatures, performs signal processing, and generates gain control commands to the low-noise amplifying unit.

14. The apparatus for detecting sodium in a liquid according to claim 13, wherein the signal-processing and controlling unit includes a measurement-condition setting unit configured to set a sodium-concentration measurement range to a required range.

15. The apparatus for detecting sodium in a liquid according to claim 13, wherein the signal-processing and controlling unit includes a measurement-status display unit configured to display the measured concentration of the sodium, the measured temperature, and the electrode voltage that is processed by the microcomputer.

16. The apparatus for detecting sodium in a liquid according to claim 13, wherein the signal-processing and controlling unit includes a communication circuit configured to transmit measured sodium concentration received from the filtering and amplifying unit or a measured liquid temperature received from the filtering and amplifying unit to an external equipment using analog or digital methods.

* * * * *